US009356405B1

(12) United States Patent
Skagmo

(10) Patent No.: US 9,356,405 B1
(45) Date of Patent: May 31, 2016

(54) CONNECTOR TONGUE ELEMENT FOR AN ELECTRICAL CONNECTOR PLUG RECEPTACLE AND A METHOD FOR PRODUCING THE SAME

(71) Applicant: Sony Corporation, Tokyo (JP)

(72) Inventor: Daniel Skagmo, Malmö (SE)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/639,468

(22) Filed: Mar. 5, 2015

(51) Int. Cl.
*H01R 12/24* (2006.01)
*H01R 13/66* (2006.01)
*H01R 43/20* (2006.01)
*H01R 13/52* (2006.01)

(52) U.S. Cl.
CPC .......... *H01R 13/665* (2013.01); *H01R 13/5202* (2013.01); *H01R 43/205* (2013.01)

(58) Field of Classification Search
CPC ...... H01R 12/79; H01R 12/592; H01R 12/78; H01R 23/662; H01R 43/24
USPC .................................. 439/492–499, 604, 606
See application file for complete search history.

(56) References Cited

U.S. PATENT DOCUMENTS 3,278,887 A 10/1966 Travis
4,030,799 A * 6/1977 Venaleck ............. H01R 12/675 439/405
4,094,564 A * 6/1978 Cacolici ............... H01R 23/662 439/456
4,260,209 A * 4/1981 Zell ...................... H01R 12/675 29/842
5,762,521 A * 6/1998 Tanaka ................. H01R 12/777 439/492
6,305,970 B1 * 10/2001 Nagai .................. H01R 12/592 439/422
6,468,106 B2 * 10/2002 Durocher ............... H01R 12/62 439/493
7,223,120 B2 * 5/2007 Ko ......................... H01R 13/26 439/492
7,261,569 B2 * 8/2007 Uchida .................. H05K 3/365 439/492
8,083,541 B2 * 12/2011 Yeh ........................ H01R 4/023 439/492
8,398,427 B2 * 3/2013 Wu .......................... H01R 4/02 439/497
8,794,995 B2 * 8/2014 Wu ...................... H01R 12/598 439/497
8,801,457 B2 * 8/2014 Nomura ............... H01R 12/613 439/492
9,017,094 B2 * 4/2015 Ikeda .................. H01R 12/592 174/117 F (Continued)

FOREIGN PATENT DOCUMENTS

EP 2 706 626 A1 3/2014

OTHER PUBLICATIONS

International Search Report, Application No. PCT/IB2015/056394, Nov. 20, 2015.

*Primary Examiner* — Thanh Tam Le
(74) *Attorney, Agent, or Firm* — Myers Bigel & Sibley, P.A.

(57) ABSTRACT

A connector tongue element for a plug receptacle includes a flexible printed circuit. Connector pins are electrically connected to the flexible printed circuit at an attachment portion. A first body of polymeric material is molded around to mechanically secure at least a part of the attachment portion to form a connector base portion. The connector pins extend from the connector base portion in a withdrawal direction along which an electrical connector plug can be withdrawn from the plug receptacle. The connector pins form a connector tongue portion extending from the connector base portion in the withdrawal direction. The first body allows the connector pins to present connecting surfaces for connecting the plug receptacle to the electrical connector plug. The connector base portion includes electronic circuitry to monitor status of electric connections within the plug receptacle, and the first body is molded around the electronic circuitry.

10 Claims, 3 Drawing Sheets

12
12
12
12
12
18
10
14
13

(56) References Cited

U.S. PATENT DOCUMENTS

2005/0059273 A1 3/2005 Chiou et al.
2010/0216341 A1 8/2010 Bryant-Rich
2013/0337688 A1 12/2013 Zong et al.

* cited by examiner

CONNECTOR TONGUE ELEMENT FOR AN ELECTRICAL CONNECTOR PLUG RECEPTACLE AND A METHOD FOR PRODUCING THE SAME

TECHNICAL FIELD

The present invention relates to an electrical connector, especially a connector tongue element for an electrical connector plug receptacle. The present invention also relates to a method of producing the connector tongue element for an electrical connector plug receptacle.

BACKGROUND

Electrical connectors are used in a wide variety of applications. One type of electrical connectors is connectors comprising a receptacle and a plug arranged to be inserted into the receptacle in order to achieve an electrical connection between one or more contacts. The receptacle may e.g. be arranged in an electrical device such a mobile phone, a tablet, a PDA, a laptop, a smart watch or smart glasses. The electrical connector may be used for e.g. charging a battery of the electrical device or transferring data to and/or from the electrical device. The receptacle may comprise a connector tongue element comprising connector pins used for connecting the receptacle with corresponding connector surfaces of the plug. One type of electrical connectors having such a receptacle comprising a connector tongue element is the micro-USB electrical connector.

In the electrical device the connector tongue element of the receptacle is in electrical contact a printed circuit of the electrical device. This typically made by soldering or by other means electrically connecting the connector tongue element to the printed circuit. During use of the electrical device the electrical contact between the connector tongue element and the printed circuit may be degraded. Hence, there is a need for improvements in the electrical contacting of the receptacle with the printed circuit of the electrical device.

SUMMARY OF THE INVENTION

In view of the above, it is an object of the present invention to provide a improved connector tongue element for an electrical connector plug receptacle.

According to a first aspect a connector tongue element for an electrical connector plug receptacle is provided. The connector tongue element comprising: a flexible printed circuit having an attachment portion; connector pins attached and electrically connected to the flexible printed circuit at the attachment portion; and a first body of polymeric material molded around at least a part of the attachment portion to form a connector base portion, the first body mechanically secures the attachment of the connector pins to the flexible printed circuit. Wherein the connector pins extend from the connector base portion in a withdrawal direction along which an electrical connector plug is adapted to be withdrawn from the electrical connector plug receptacle. Wherein the connector pins form a connector tongue portion extending from the connector base portion in the withdrawal direction. Wherein the first body allow the connector pins to present connecting surfaces for connecting the electrical connector plug receptacle to the electrical connector plug.

The first body of polymeric material mechanically securing the attachment of the connector pins to the flexible printed circuit provide for a stable and persistent electrical contacting between the flexible printed circuit and the connector pins.

Accordingly, by integrating the flexible printed circuit into the connector tongue element lifetime of the electrical contacting within an electronic device comprising the electrical connector plug receptacle is enhanced.

The connector tongue portion may further comprise a second body of polymeric material molded along the connector pins, the second body mechanically secures the connectors pins relative each other. The second body of polymeric material will even further enhance the lifetime of the electrical contacting within an electronic device comprising the electrical connector plug receptacle. This since the mechanically securing of the connectors pins relative each other will make the connector tongue element more stable. Moreover, by mechanically securing the connectors pins relative each other short circuits in the connector tongue element due to relative movement of the connectors pins is prevented.

The first and second bodies may be integrally formed.

The connector pins may be partly embedded in the second body.

The first body may be molded around the flexible printed circuit and the connector pins such that the connector base portion forms a sealing body around and sealingly connected to the flexible printed circuit and the connector pins. This will prevent dust and/or water to enter the electronic device via an interface between the flexible printed circuit and the connector base portion. Hence, it will be possible to provide a water proofed electrical connector plug receptacle.

The sealing body may be adapted to abut a sealing surface extending around a through-opening in a housing forming part of the electrical connector plug receptacle. This will prevent dust and/or water to enter the electronic device via an interface between the connector base portion and the housing of the electrical connector plug receptacle. Hence, it will be possible to provide a water proofed electrical connector plug receptacle.

The flexible printed circuit may be adapted to extending through the through-opening in the housing forming part of the electrical connector plug receptacle.

The connector base portion may further comprise electronic circuitry adapted to monitor status of electric connections within the electrical connector plug receptacle, wherein the first body is molded around the electronic circuitry. By embedding electronic circuitry within the first body, i.e. the connector base portion, space on the flexible printed circuit not being part of the connector tongue element of the electrical connector plug receptacle may be saved. Hence, a smaller flexible printed circuit may be used saving space in the electrical device comprising the electrical connector plug receptacle.

The electronic circuitry may be arranged for sensing a temperature of the connector tongue element. This allow for detection of short circuits within the electrical connector plug receptacle. Such short circuits may lead to a potential hazard of fire. Hence, such hazards may be avoided by sensing the temperature.

The first body may enclose the electronic circuitry.

The electrical connector plug receptacle may be a micro USB receptacle. The electrical connector plug may be a micro USB plug.

According to a second aspect a method of producing a connector tongue element for an electrical connector plug receptacle is provided. The method comprising: attaching connector pins to a flexible printed circuit at an attachment portion of the flexible printed circuit such that the connector pins are electrically connected to the flexible printed circuit at the attachment portion; and molding a first body of polymeric material around at least a part of the attachment portion to form a connector base portion such that the first body mechanically secure the attachment of the connector pins to the flexible printed circuit and such that the first body allow the connector pins to present connecting surfaces for connecting the electrical connector plug receptacle to an electrical connector plug.

The method may further comprise molding a second body of polymeric material along the connector pins such that the connectors pins are mechanically secured relative each other.

The above mentioned features of the connector tongue element, when applicable, apply to this second aspect as well. In order to avoid undue repetition, reference is made to the above.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles “a,” “an,” “the,” and “said” are intended to mean that there are one or more of the elements unless the context clearly dictates otherwise. Thus, for example, reference to “a unit” or “the unit” may include several devices, and the like. Furthermore, the words “comprising”, “including”, “containing” and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

Figure 1:
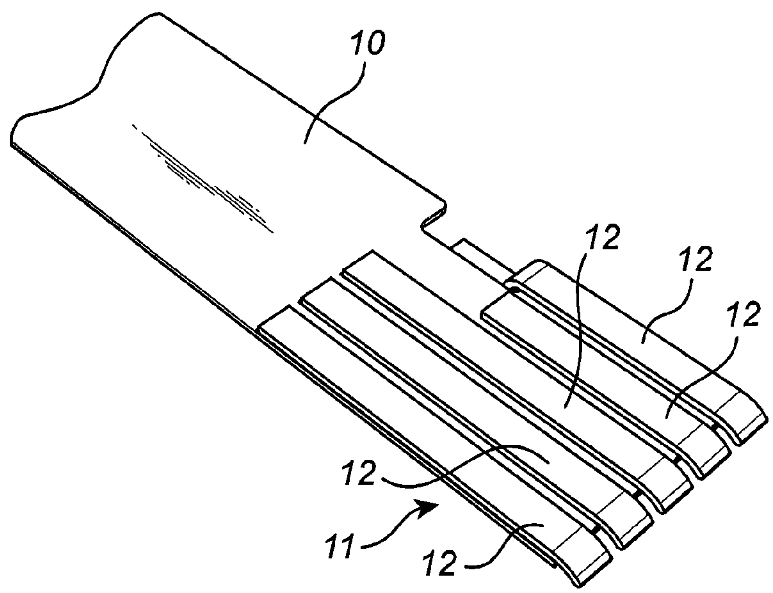
FIG. 1 is schematic view a flexible printed circuit with a plurality of contact pins attached and electrically connected thereto.

FIG. 1 illustrates a flexible printed circuit 10 with a plurality of contact pins 12 attached and electrically connected thereto. The contact pins 12 are attached to the flexible printed circuit 10 at an attachment portion 11 thereof. The flexible printed circuit 10 together with the contact pins 12 provides a starting point for producing a connector tongue element for an electrical connector plug receptacle. The contact pins 12 may e.g. be contact pads. The contact pins 12 may be soldered to the flexible printed circuit 10. However, other methods for attaching the contact pins 12 to the flexible printed circuit may as well be used.

Figure 2A:
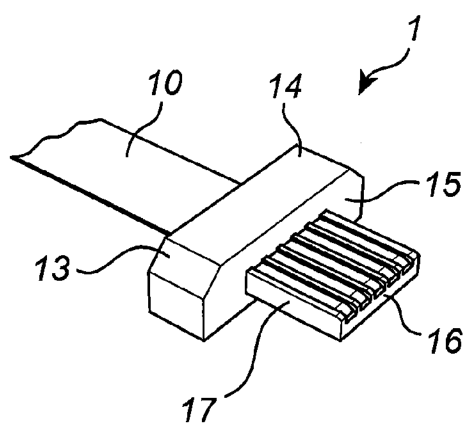
FIGS. 2*a* and 2*b* are schematic views of a connector tongue element for an electrical connector plug receptacle.
Figure 2B:
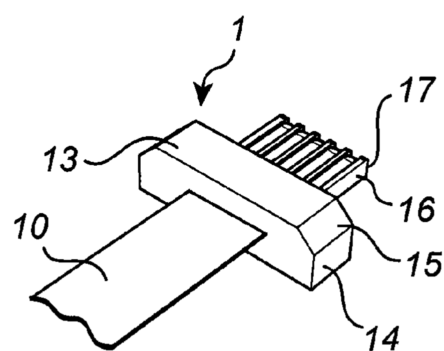

FIGS. 2*a* and 2*b* illustrates a connector tongue element 1 for an electrical connector plug receptacle 4 seen from different perspectives. The connector tongue element 1 comprises the flexible printed circuit 10 with the plurality of contact pins 12 attached and electrically connected thereto from FIG. 1 and a body 15 of polymeric material molded around the attachment portion 11 of the flexible printed circuit 10. The attachment portion 11 of the flexible printed circuit 10, the connector pins 12 and the body 15 integrally form the connector tongue element 1. The body 15 of polymeric material comprises two portions; a first body 13 of polymeric material molded around at least a part of the attachment portion 11 to form a connector base portion 14, and a second body 17 of polymeric material molded along the connector pins 12. The first body 13 mechanically secures the attachment of the connector pins 12 to the flexible printed circuit 10. Moreover, the first body 13, i.e. the connector base portion 14, sealingly connects the flexible printed circuit 10 and the connector pins 12. The second body 17 mechanically secures the connectors pins 12 relative each other. The connector pins 12 are partly embedded in the second body 17. The first and second bodies 13, 17 may be integrally formed.

Figure 3A:
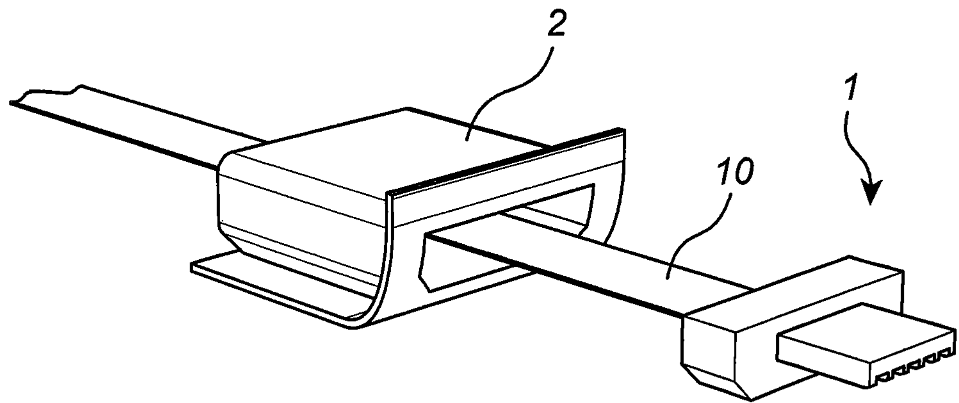
FIGS. 3*a*-3*c* illustrates the insertion of the connector tongue element of FIGS. 2*a* and 2*b* into a housing of the electrical connector plug receptacle.
Figure 3B:
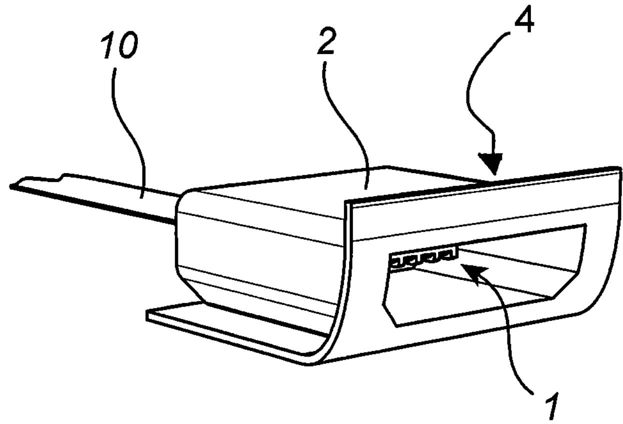
Figure 3C:
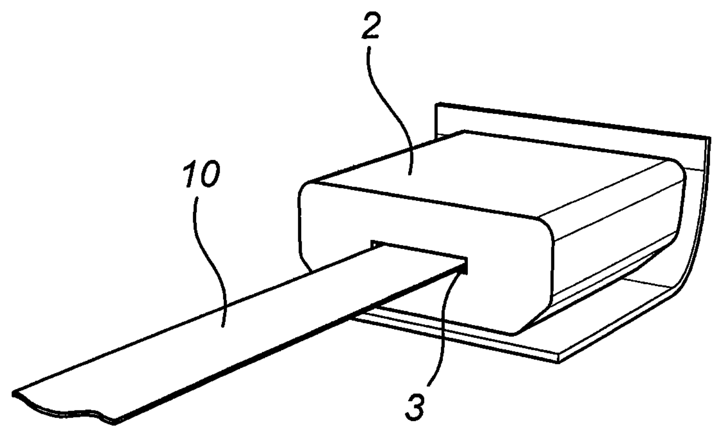

FIGS. 3*a*-3*c* illustrates the insertion of the connector tongue element 1 of FIGS. 2*a* and 2*b* into a housing 2 of the electrical connector plug receptacle 4. The housing 2 may e.g. be formed as a part of a shell of an electrical device comprising the electrical connector plug receptacle 4. From FIGS. 3*a*-3*c* it can be seen that the sealing body provided by the connector base portion 14 is adapted to abut a sealing surface extending around a through-opening 3 in the housing 2. When the connector tongue element 1 is inserted into the housing 2 the flexible printed circuit 10 is extending through the through-opening 3. After inserting the connector tongue element 1 into the housing 2 the through-opening 3 may be sealed adding some kind of sealant, e.g. sealing glue.

Figure 4:
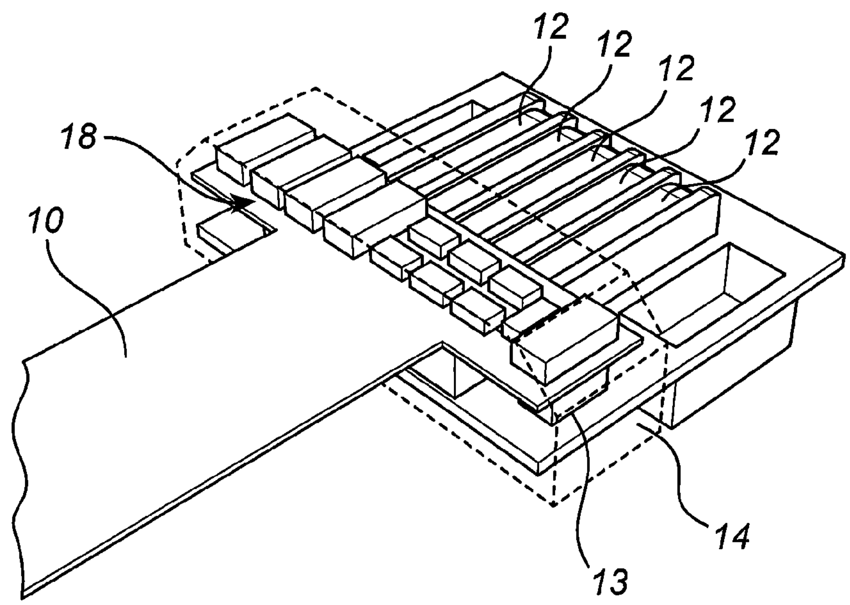
FIG. 4 illustrates an alternative embodiment of the connector tongue element for an electrical connector plug receptacle.

FIG. 4 illustrates an embodiment of the connector tongue element 1 for the electrical connector plug receptacle. In this embodiment the connector base portion 14 further comprises electronic circuitry 18. The electronic circuitry 18 is adapted to monitor status of electric connections within the electrical connector plug receptacle. The first body 13 is molded around the electronic circuitry 18. The first body 13 encloses the electronic circuitry 18. By embedding electronic circuitry 18 within the connector base portion 14 space on the flexible printed circuit 10 to be used for other kind of electronic circuitry may be saved. Hence, a smaller flexible printed circuit 10 may be used saving space in the electrical device comprising the electrical connector plug receptacle 4.

It has been found that there might be a problem with foreign materials, such as water, dust etc., getting into the electrical connector plug receptacle 4. This might create a short circuit within the electrical connector plug receptacle 4. Such short circuits leads to increased temperatures within the electronic device comprising the electrical connector plug receptacle 4 with a potential hazard of fire. The above embodiment embedding electronic circuitry 18 within the connector base portion 14 allow for temperature sensing of the electrical connector plug receptacle 4. By embedding electronic circuitry 18 for sensing the temperature of the electrical connector plug receptacle 4 within the connector base portion 14 otherwise useless space of the flexible printed circuit may be used saving the space on the flexible printed circuit outside the connector base portion 14 for other kind of electronic circuitry. There is also a benefit locating the temperature sensing electronic circuitry in close proximity of the electrical connector plug receptacle 4.

Figure 5:
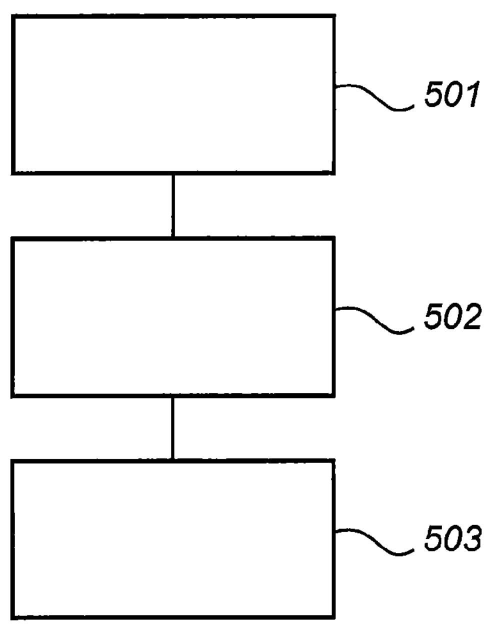
FIG. 5 is block diagram of the producing of the connector tongue element.

In FIG. 5 a schematic block diagram illustrating a method of producing the connector tongue element for the electrical connector plug receptacle. The method comprising: attaching 501 connector pins to the flexible printed circuit at an attachment portion of the flexible printed circuit such that the connector pins are electrically connected to the flexible printed circuit at the attachment portion; and molding 502 a first body of polymeric material around at least a part of the attachment portion to form a connector base portion such that the first body mechanically secure the attachment of the connector pins to the flexible printed circuit and such that the first body allow the connector pins to present connecting surfaces for connecting the electrical connector plug receptacle to an electrical connector plug. The method may further comprise molding 503 a second body of polymeric material along the connector pins such that the connectors pins are mechanically secured relative each other. The two steps of molding 502 and 503 may be combined into a single step.

The person skilled in the art realizes that the present invention by no means is limited to the preferred embodiments described above. On the contrary, many modifications and variations are possible within the scope of the appended claims.

For example, first and second bodies 15, 17 may be formed as separate bodies.

Moreover, the electronic circuitry 18 embedded in the first body 15 of polymeric material, i.e. the connector base portion 14, may have other functions as well.

Additionally, variations to the disclosed embodiments can be understood and effected by the skilled person in practicing the claimed invention, from a study of the drawings, the disclosure, and the appended claims.

The invention claimed is:

1. A connector tongue element for an electrical connector plug receptacle, the connector tongue element comprising:

a flexible printed circuit having an attachment portion;

connector pins attached and electrically connected to the flexible printed circuit at the attachment portion; and a first body of polymeric material molded around at least a part of the attachment portion to form a connector base portion, the first body mechanically secures the attachment of the connector pins to the flexible printed circuit;

wherein the connector pins extend from the connector base portion in a withdrawal direction along which an electrical connector plug is adapted to be withdrawn from the electrical connector plug receptacle;

wherein the connector pins form a connector tongue portion extending from the connector base portion in the withdrawal direction;

wherein the first body allow the connector pins to present connecting surfaces for connecting the electrical connector plug receptacle to the electrical connector plug; and wherein the connector base portion further comprises electronic circuitry adapted to monitor status of electric connections within the electrical connector plug receptacle, wherein the first body is molded around the electronic circuitry.

2. The connector tongue element according to claim 1, wherein the connector tongue portion further comprises a second body of polymeric material molded along the connector pins, the second body mechanically secures the connectors pins relative each other.

3. The connector tongue element according to claim 2, wherein the first and second bodies are integrally formed.

4. The connector tongue element according to claim 2, wherein the connector pins are partly embedded in the second body.

5. The connector tongue element according to claim 1, wherein the first body is molded around the flexible printed circuit and the connector pins such that the connector base portion forms a sealing body around and sealingly connected to the flexible printed circuit and the connector pins.

6. The connector tongue element according to claim 5, wherein the sealing body is adapted to abut a sealing surface extending around a through-opening in a housing forming part of the electrical connector plug receptacle.

7. The connector tongue element according to claim 6, wherein the flexible printed circuit is adapted to extending through the through-opening in the housing forming part of the electrical connector plug receptacle.

8. The connector tongue element according to claim 1, wherein the first body encloses the electronic circuitry.

9. The connector tongue element according to claim 1, wherein the electrical connector plug receptacle is a micro USB receptacle and wherein the electrical connector plug is a micro USB plug.

10. The connector tongue element according to claim 1, wherein the electronic circuitry is configured for sensing the temperature of the electrical connector plug receptacle.

* * * * *